(12) United States Patent
Hansen et al.

(10) Patent No.: US 10,195,401 B2
(45) Date of Patent: Feb. 5, 2019

(54) WIRE GUIDE FOR TRAVERSING BODY PASSAGES

(71) Applicant: Cook Medical Technologies LLC, Bloomington, IN (US)

(72) Inventors: Palle Munk Hansen, Bjaeverskov (DK); Steen Aggerholm, Bjaelkerupvej (DK); Per Hendriksen, Herlufmagle (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 405 days.

(21) Appl. No.: 14/868,827

(22) Filed: Sep. 29, 2015

(65) Prior Publication Data

US 2016/0089515 A1 Mar. 31, 2016

Related U.S. Application Data

(60) Provisional application No. 62/056,686, filed on Sep. 29, 2014.

(51) Int. Cl.
*A61M 25/09* (2006.01)

(52) U.S. Cl.
CPC ..... *A61M 25/09* (2013.01); *A61M 2025/0915* (2013.01); *A61M 2025/09075* (2013.01); *A61M 2025/09166* (2013.01); *A61M 2205/0288* (2013.01)

(58) Field of Classification Search
CPC .......... A61M 25/09; A61M 2025/0915; A61M 2025/09075; A61M 2025/09166; A61M 2205/0288
See application file for complete search history.

(56) References Cited

U.S. PATENT DOCUMENTS

| | | | |
|---|---|---|---|
| 4,054,128 A | 10/1977 | Seufert et al. | |
| 5,605,162 A * | 2/1997 | Mirzaee | A61M 25/09 128/898 |
| 5,827,201 A | 10/1998 | Samson et al. | |
| 5,902,254 A * | 5/1999 | Magram | A61M 25/09 600/585 |
| 6,113,557 A | 9/2000 | Fagan et al. | |
| 6,287,292 B1 | 9/2001 | Fariabi | |
| 6,638,266 B2 | 10/2003 | Wilson et al. | |
| 6,884,225 B2 | 4/2005 | Kato et al. | |
| 6,974,411 B2 | 12/2005 | Belson | |
| 7,413,543 B2 | 8/2008 | Banik et al. | |
| 7,867,176 B2 | 1/2011 | Wu et al. | |
| 7,993,285 B2 | 8/2011 | Eskuri | |
| 8,372,017 B2 | 2/2013 | Schiff et al. | |

(Continued)

FOREIGN PATENT DOCUMENTS

EP 0410557 A2 2/1990

*Primary Examiner* — Amber Stiles
(74) *Attorney, Agent, or Firm* — Brinks Gilson & Lione

(57) ABSTRACT

A wire guide for feeding a medical catheter through the body passage of a patient to a distant target site within the body has a variably flexible distal portion. The distal portion facilitates threading the guidewire in a tortuous path through acute bends at branch junctions in the body passages of the patient. The wire guide end is able to feed into very delicate vessels such as ventricles of the brain and the spinal canal without puncturing the wall or damaging organs.

20 Claims, 3 Drawing Sheets

(56) References Cited

U.S. PATENT DOCUMENTS

| | | |
|---|---|---|
| 8,372,074 B2 | 2/2013 | Milbank |
| 8,376,963 B2 | 2/2013 | Wright et al. |
| 2006/0079812 A1* | 4/2006 | Viswanathan ........ A61M 25/09 600/585 |
| 2007/0149951 A1* | 6/2007 | Wu ....................... A61M 25/09 604/526 |
| 2008/0077119 A1* | 3/2008 | Snyder .............. A61M 25/0051 604/525 |

* cited by examiner

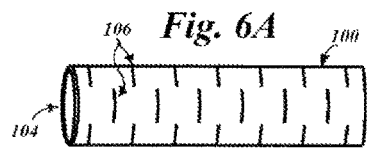 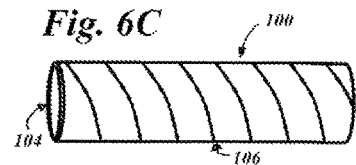
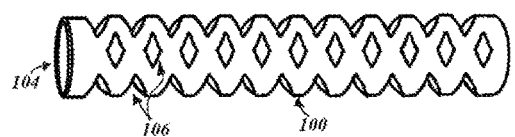 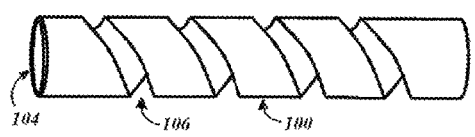
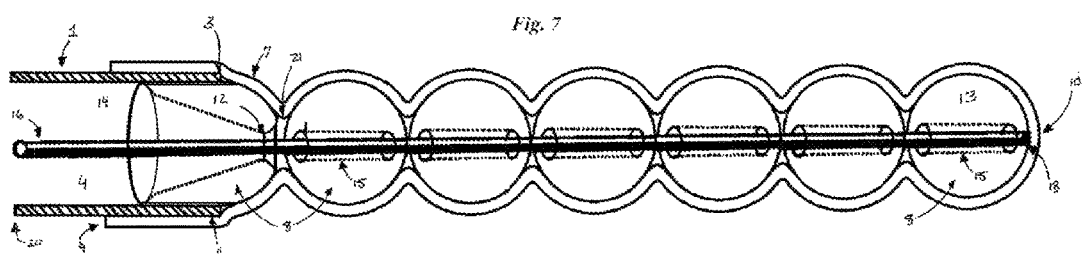

WIRE GUIDE FOR TRAVERSING BODY PASSAGES

CROSS-REFERENCE TO RELATED APPLICATIONS

This application claims the benefit of U.S. Provisional Application No. 62/056,686 filed on Sep. 29, 2014, entitled "WIRE GUIDE FOR TRAVERSING BODY PASSAGES," the entire contents of which are incorporated herein by reference.

FIELD OF THE INVENTION

The present invention generally relates to medical devices and, more particularly, to medical devices employed for navigating tortuous body passages atraumatically.

BACKGROUND OF THE INVENTION

Wire guides are used in a variety of medical procedures involving the vasculature of a patient.

Wire guides can be described as elongated flexible members used to provide a path along which another medical device can be moved. For example, the path provided by the wire guide can be used to navigate a medical device, such as a catheter, through a body vessel.

The catheter and wire guide are often highly flexible in order to traverse the tortuous body passages en route to the treatment location. Such wire guides are advanced through the circulatory system by applying a torque to the proximal end of the wire guide at an external site. In this example, the wire guide has sufficient column strength to allow the distal end of the wire guide to be manipulated from the external access site.

Current catheter wire guide designs attempt to meet these requirements by incorporating a number of features designed to increase the flexibility of the distal end of the wire guide while maintaining torsional rigidity. Such designs may include a tapered distal end region of the wire guide.

However, such tapering may reduce the torsional rigidity of the wire guide, resulting in additional manufacturing steps which may be more time consuming or complex.

SUMMARY OF THE INVENTION

Embodiments of the present invention provide a wire guide having enhanced torsional rigidity, enhanced flexibility, and reduced manufacturing complexity.

According to one aspect of the present invention, a wire guide to access a body vessel of a patient is provided. The wire guide comprises a cannula having a proximal end and a distal end. The cannula has a first lumen formed through the proximal and distal ends, and the cannula has a plurality of cuts to allow the cannula to extend, defining variable rigidity. The wire guide also comprises a flexible portion comprising a covering and a plurality of members disposed in the covering. The covering has an open end extending to a closed end. The open end is attached about the distal end of the cannula. The plurality of members includes a first body attached to the distal end of the cannula and a second body disposed at the closed end of the covering. The members have apertures defining a second lumen in axial alignment with the first lumen. The wire guide also comprises a core wire having a distal tip and being slidably disposed through the first lumen and the second lumen. The distal tip is attached to the second body.

In accordance with another aspect of the present invention, one embodiment comprises an assembly of the wire guide for accessing a body vessel. The assembly includes the wire guide and an outer sheath having a proximal section extending to a distal section. The outer sheath has a sheath lumen formed therein through the proximal and distal sections. The wire guide is disposed within the sheath lumen and the outer sheath is configured to translate axially relative to the wire guide.

In accordance with yet another aspect of the present invention, a method of accessing a body vessel is provided. The method comprises providing the assembly, introducing the outer sheath to the body vessel, inserting a wire guide through the outer sheath, varying the rigidity of the cannula, and navigating the wire guide through the body vessel to a treatment location.

Further aspects, features, and advantages of the invention will become apparent from consideration of the following description and the appended claims when taken in connection with the accompanying drawings.

DESCRIPTION OF THE DRAWINGS

FIGS. 6A and 6B are partial side views of the plurality of cuts in the cannula in accordance with one embodiment of the present invention, wherein the cuts are unextended and extended respectively.

FIGS. 6C and 6D are partial side view of the plurality of cuts in the cannula in accordance with another embodiment of the present invention, wherein the cuts are unextended and extended, respectively.

FIG. 7 is a partial sectional view of the flexible portion having a first body in accordance with one embodiment of the present invention.

DETAILED DESCRIPTION

Figure 1:
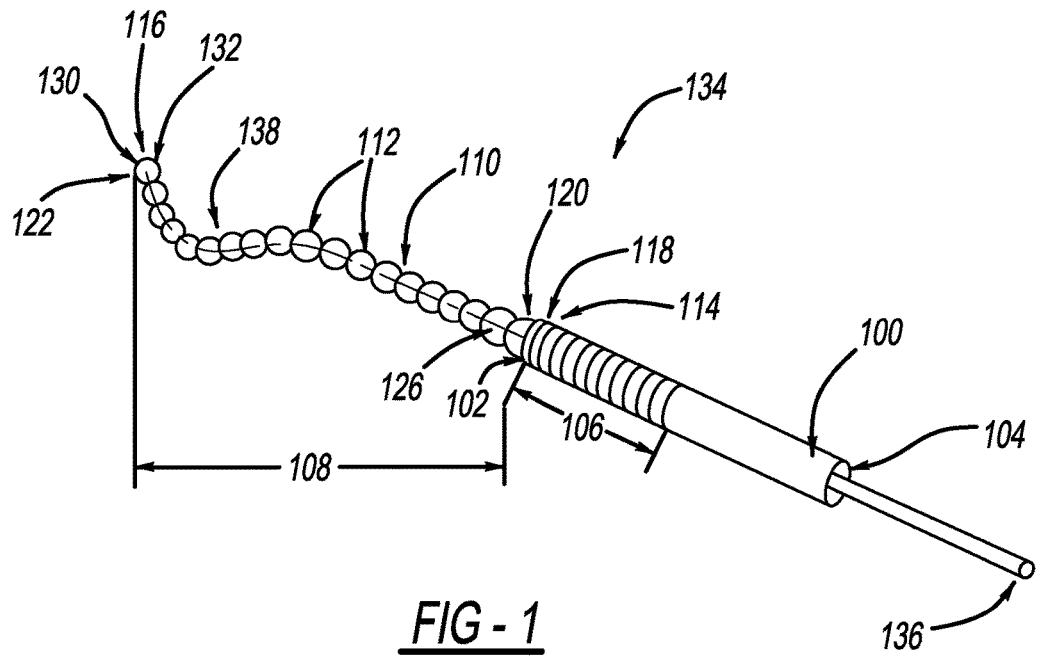
FIG. 1 is a perspective view of the wire comprising a cannula having a plurality of cuts in accordance with one embodiment of the present invention.

In this description, when referring to a deployment or treatment assembly, the term distal is used to refer to an end of a component which in use is furthest from the clinician during the medical procedure, including within a patient. The term proximal is used to refer to an end of a component closest to the clinician and in practice in or adjacent to an external manipulation part of the deployment or treatment apparatus.

The novel wire guide 134 includes a cannula portion 100, a flexible portion 108, and a core wire 128. The cannula portion 100 includes a series of cuts 106 to provide it with variable length. The flexible portion 108 includes a number of spheroidal members 112 that are displaced longitudinally at the distal end of a core wire 128 and within a covering 110. The core wire 128 is displaced internally to both the cannula portion 100 and the beaded portion 108, passing through a first lumen 104 within the cannula 100, and a second lumen 126 defined by the apertures 124 in each of the spheroidal members 112. The core wire 128 is affixed to the distal-most member 122. The members 112 are separated from one another by variable gap distances 138 manipulated to alter the flexibility of the distal portion of the core wire. The core wire 128 can flex at points within the gaps 138 between the member 112 which allows the distal end 108 of the wire guide to bend at branch junctions and to conform to the curvature in the vessel duct. The member 112 can be fixed to the core wire 128 or they can move freely along the distal portion of the core wire 108. Also, member 112 freely sliding along the core wire 128 may be compressed against one another to control the flexibility and curvature of the distal portion 108 by manipulating the proximal end 136 of the core wire and inducing varying amounts of tension in cannula portion 100, and thereby the flexible portion 6, of the wire guide 134. Finally, the covering element 110 is disposed about the beaded portion 108 of the wire guide 134 and extends from a closed end 116 about the distal-most member 122 to the distal end of the cannula portion 102, where it is affixed about 118 the distal end of the cannula 102. An insertion tube is provided for initially feeding the flexible wire guide end into the body passage.[LK1]

A first embodiment of the invention can be understood with reference to FIG. 1. The catheter wire guide 134 has a core wire 128 having a length to reach a distant target site when fed percutaneously from outside the body into the lumen of a bodily duct. The wire guide has a proximal end 136 that remains outside the body and is manipulated by a physician. Generally, the core is flexible so as to be capable of threading through a branched bodily duct network along a tortuous path. The thickness, shape of cross section, and materials of construction of the core wire can vary along the length to provide different mechanical properties, such as flexibility and torsional strength. Preferably, near or adjacent the proximal end, the core wire may be relatively stiff. Moreover, the core wire near the proximal end may be relatively stiff. Preferably, the proximal portion of the wire guide is less flexible because it usually resides in larger diameter, slightly curving sections of the duct network near the entry point. Also the increased stiffness near the proximal end facilitates transmission of torque along the full length of the wire guide to aid in steering the tip at the distal end. Preferably, wire guide flexibility increases along the length toward the distal end.

Throughout this specification reference will be made to a plurality of cuts 106 and a plurality of members 112. Unless otherwise stated, the term "cuts" shall hereinafter refer to a plurality of incisions on the cannula 100 which may be in any patterns designed to allow for longitudinal expansion and contraction of the cannula 100. Additionally, the term "members" shall hereinafter refer to a plurality of structures disposed between the distal end of the cannula 102 and the distal tip of the core wire 130; where the members 112 can be any shape with rounded edges that allow for movement against one another and smooth passage through the body duct. For example, each of the plurality of members 112 could be spherical, ovoid, ring-like, or any combination of such shapes or any other such rounded shape. The embodiments of this invention include at least two members. The at least first member 120 is affixed to the distal end of the cannula 102, and a second member 122 is affixed to the distal tip 130 of the core wire 128 at an attachment region 132.

At its distal end, the core wire terminates at tip 130 on which is affixed a second member 122. Because the second member 122 at the distal tip of the core wire 130 leads the wire guide through the bodily duct, the second member 122 is a blunt form to reduce the risk of wall penetration. The second member 122 can have a spheroidal shape. The term "spheroidal" means that the shape can be imperfectly spherical as well as exactly spherical. Spheroidal shapes can include spherical, elliptical, ovoid, and hemi-spheroidally-ended cylindrical shapes, as well as ring-like structures and round-ended semi-cylindrical structures. If conical, the forward and trailing ends should be blunted to remove any sharp edges which could provide a risk of penetration of the duct walls.

To assure that the second member 122 does not separate from the core wire 128, the second member 122 should be securely attached to the distal tip 130 of the core wire. The method of attachment is not critical to operation of the invention. For example, the second member 122 and the core wire 128 could be manufactured as a single piece, the second member 122 thereby being integral to the core wire 128. Alternative exemplary methods of attachment including cementing, thermally fusing, or crimping the second member 122 to the core wire 128, fastening with clamps, pins and set screws, and any combination of these.

The flexible portion 108 of the wire guide includes a plurality of spheroidal members 112 positioned sequentially along the core wire 128. The members 112 are slidably disposed along the core wire 128 such that they can move relative to one another. The flexible portion 108 of the wire guide also includes a covering 110 having a closed end 116 at the distal tip 130 of the core wire, and an open end 114 that extends about, and is affixed to, the distal end 102 of the cannula 100. The covering 110 encases the members 112, such that they are prevented from separating from the core wire 128 and drifting through the patient's vasculature. The members 112 also generally have smooth, rounded surfaces to prevent drag against the covering 110 or the duct walls during wire guide movement within the duct lumen.

The flexible portion 108 of the wire guide is intended to lead the wire guide into the usually very small duct branches in the far reaches of the network. Consequently, the diameter of the members 112 should be sufficiently small for the flexible portion 108 to slide easily through the narrowest ducts.

The members 112 are spaced apart along the axis of the core wire 128 by a small distance which creates a gap 138 between adjacent members 112. The core wire 128 can flex freely in the gaps. Such flexing permits the distal portion to assume suitable curvature to advance the distal end of the device toward the target site through acute curves in a body duct network. Furthermore, the gap 138 between members 112 is variable, and may be reduced such that the members 112 are touching one another, and the wire guide 134 is thereby stiffened. It is important that the flexible portion 108 not be too flexible, as under such a configuration, it could kink and jam within the body duct.

Members 112 of the novel wire guide will also be defined by a characteristic length. References to "length" should be interpreted to mean the maximum axial dimension of a member, such as the dimension 140 in FIG. 3, FIG. 4 and FIG. 5. The aspect ratio of the members, that is, the ratio of the length relative to the diameter, can also influence the ability of the flexible portion to fold, kink, or jam within the body duct. Members with too great an aspect ratio will cause the flexible portion to function as a straight, rigid rod, rather than a flexible wire guide. While this could be beneficial, in some embodiments, for navigating stenosed regions of the vasculature, such members would be incapable of navigating sharp curves within the patient's body ducts. Conversely, if the aspect ratio of the members is too small, the members may tend to bunch together and jam in the duct at bends or branch junctions. Therefore, a variety of embodiments are contemplated such that the physician may choose a device with the appropriate flexibility and navigability characteristics for the particular procedure.

Some or all of the members 112 may also have magnetic properties, radiopaque characteristics, or both. Members with radiopaque characteristics can be seen by using imaging technology known in the art, and can aid physicians in properly placing the wire guide 134 within the body of a patient. With reference to guidance, in some embodiments of the invention, some or all of the members 112 may have magnetic properties as well. In this invention, the term "magnetic" is used to refer to a composition that is a permanent magnet, a paramagnetic material, a diamagnetic material, or any other form of magnetic material. In instances where some or all of the members 112 comprise a magnetic material, the magnetic material can be used to assist a physician in guiding the wire guide 134 through the body of a patient. This may be accomplished by applying attractive or repulsive magnetic fields generated outside the body of the patient to the magnetic members 112 of the wire guide 134.

In some preferred embodiments of the invention only repulsive magnetic fields will be applied to members 112 of the wire guide 134 which have magnetic properties. In such cases, since the magnetic field strength falls off exponentially with the distance to the source, very fine control of the flexible portion 108 of the wire guide 134 may be accomplished.

Figure 2:
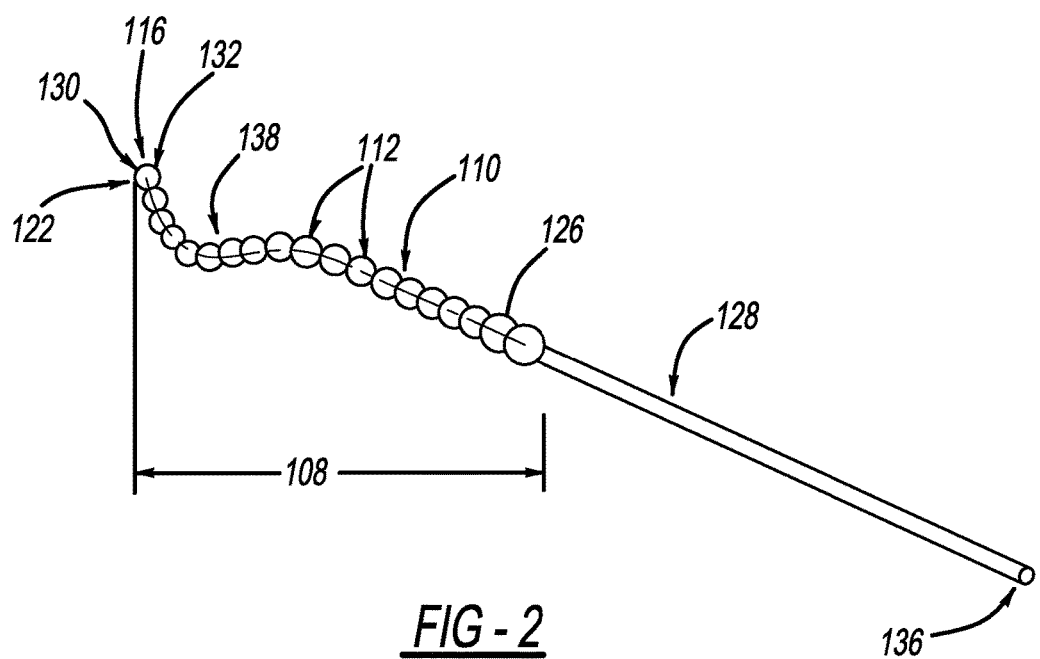
FIG. 2 is a perspective view of the wire guide comprising a core wire slidably disposed through a second lumen in accordance with one embodiment of the present invention.

FIG. 2 provides second view of the embodiment of FIG. 1, wherein the cannula 1 has been omitted so that the core wire 128 is visible along with the members 112 disposed about the flexible portion 108 of the wire guide.

Figure 3:
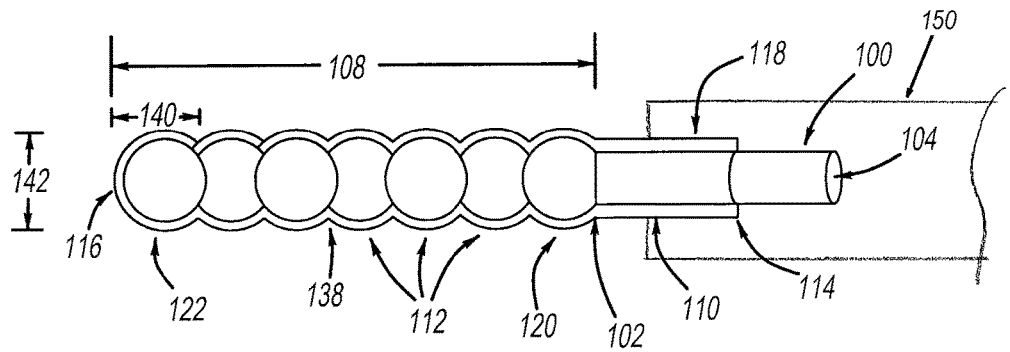
FIG. 3 is a breakaway view of the flexible portion taken along line 108 in accordance with one embodiment of the present invention.

FIG. 3 provides an enlarged view of an embodiment of the invention in which the covering 110 is shown surrounding each of the members 8, and extending from a closed end 116 at the distal-most end of the second member 122 to the distal end 102 of the cannula 100, including the entirety of the flexible portion 108. The covering 110 is further shown to encapsulate a portion of the distal end 102 of the cannula 100. This portion of the covering is affixed to the cannula 100 by clamping, gluing, bonding or any other electrical, mechanical or chemical means that is known in the art. Furthermore, the first member 120 is affixed to the distal end 102 of the cannula 100 by clamping, gluing, bonding, or any other electrical or chemical means known in the art. FIG. 3 also shows the wire guide is disposed within the lumen of an outer sheath 150, and the outer sheath 150 is configured to translate axially relative to the wire guide.

Figure 4:
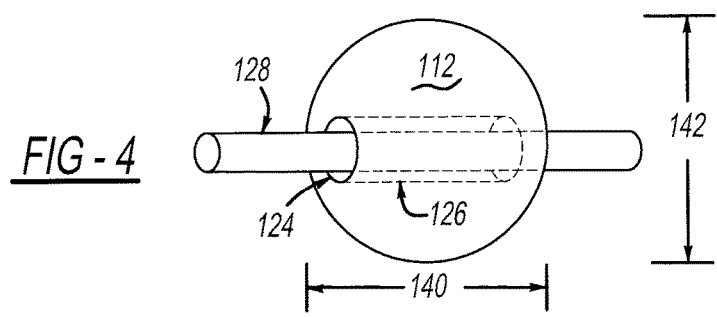
FIG. 4 is a side view of one member of the plurality of members in accordance with one embodiment of the present invention.

FIG. 4 provides an enlarged view of a single member 112 of an embodiment of the invention in which the members 112 are spherical. The core wire 128 can be seen entering and exiting the apertures 124 defining the second lumen 126 within each member 112. In this embodiment of the invention, the member 112 may slide along the core wire 128. In addition, the member 112 in this embodiment can be spheroidal with an axial length 1240 equal to its diameter. This is not limiting, however, as noted earlier, a "spheroidal" member 112 could be any shape that may be imperfectly spherical as well as exactly spherical. Spheroidal shapes can include spherical, elliptical, ovoid, and hemi-spheroidally-ended cylindrical shapes, as well as ring-like structures.

Figure 5:
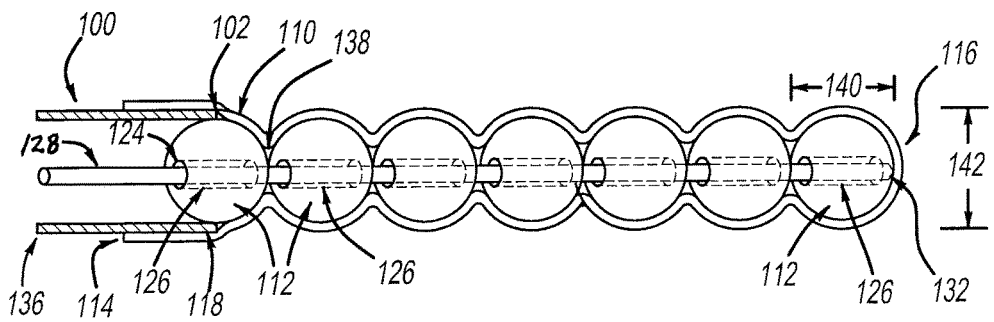
FIG. 5 is a cross sectional view of the flexible portion of wire guide in accordance with one embodiment of the present invention.

FIG. 5 depicts a partial section view of an embodiment of the invention in which the structures of FIG. 4 are incorporated into a more complete depiction of the invention. In this embodiment of the novel wire guide, the wire guide includes a slender core wire 128 extending from a proximal end 136 to a distal tip 130. The core wire 128 is affixed to the second member 122 at its distal tip 130. The attachment may be carried out by clamping, gluing, bonding, or any other electrical, mechanical or chemical means known in the art. The cannula 100 is depicted having a first lumen 104 and the members 112 are shown having apertures 124 defining a second lumen 126. The core wire 128 extends through both the first 104 and second 126 lumens, reaching from the proximal end 136 of the wire guide to the second body 122. The length of the core wire 128 can vary with each embodiment of the invention, as it will be defined in part by the number of members 112 as well as their axial lengths 140. More simply said, the length of the core wire 128 will vary with the length of the flexible portion 108 of the wire guide 134. In addition, the flexible portion 108 of the wire guide 134 can have a variable length in each embodiment, as the amount of tension applied to the core wire 128 will vary the gaps 138 between the members 112.

The covering 110 is shown having an open end 114 at the distal end 102 of the cannula and extending around each of the members 112 and terminating in a closed end 116 surrounding the second body 13. At the distal end 102 of the cannula, the open end 114 of the covering 110 is affixed in by clamping, gluing, bonding, or any other electrical, mechanical or chemical means known in the art. In this embodiment, the distal end 102 of the cannula is bonded to the open end 114 of the covering in a region denoted by the number 118.

FIG. 6A, FIG. 6B, FIG. 6C, and FIG. 6D depict partial views of two embodiments of the invention. In each of these diagrams, everything but the cannula 100 is omitted such that two different methodologies of providing cuts 106 to the cannula 100 are depicted. These depictions should not be construed as limiting, however, as they are merely intended to show that there are many methods available to provide the cannula 100 with a series of cuts 106 that create the potential for the cannula 100 to have a variable axial length.

FIG. 6A and FIG. 6B depict a series of cuts 106 in the cannula 100 such that an "scissors-lift-like" length variation may be accomplished.

FIG. 6C and FIG. 6D depict a series of cuts 106 in the cannula 100 that spiral about the cannula in such a way that a "slinky-like" length variation may be accomplished.

FIG. 7 depicts a partial section view of an alternate embodiment of the present invention, wherein the first member 120 has an alternate form, wherein the axial length 140 of the first member 120 has an axial length 140 that is different than its cross sectional diameter 142. FIG. 7 further includes the structures of FIG. 4, which are thus incorporated into a more complete depiction of the invention. In this embodiment of the novel wire guide, the wire guide includes a slender core wire 128 extending from a proximal end 136 to a distal tip 130. The core wire 128 is affixed to the second member 122 at its distal tip 130. The attachment may be carried out by clamping, gluing, bonding, or any other electrical, mechanical or chemical means known in the art. The cannula 1 is depicted having a first lumen 104 and the members 112 are shown having apertures 124 defining a second lumen 126. The core wire 128 extends through both the first 104 and second 126 lumens, reaching from the proximal end 136 of the wire guide to the second body 122. The length of the core wire 128 can vary with each embodiment of the invention, as it will be defined in part by the number of members 112 as well as their axial lengths 140. More simply said, the length of the core wire 128 will vary with the length of the flexible portion 108 of the wire guide 134. In addition, the flexible portion 108 of the wire guide 134 can have a variable length in each embodiment, as the amount of tension applied to the core wire 128 will vary the gaps 138 between the members 112.

The covering 110 is shown having an open end 114 at the distal end 102 of the cannula and extending around each of the members 112 and terminating in a closed end 116 surrounding the second body 122. At the distal end 102 of the cannula, the open end 114 of the covering 110 is affixed in by clamping, gluing, bonding, or any other electrical, mechanical or chemical means known in the art. In this embodiment, the distal end 102 of the cannula is bonded to the open end 114 of the covering in a region denoted by the number 118. In this embodiment, the first member 120, comprises an alternate form, wherein its lumen 126 has a somewhat conical cross section.

In certain aspects, the present invention provides unique wire guide devices 134 that can effectively traverse tortuous body passages atraumatically. In accordance with some forms of the invention, such wire guide devices 134 are configured to provide variable flexibility to the distal portion 108 of the device. In such devices, the wire guide 134 may include a cannula 100 provided with a series of cuts 106, a plurality of spheroidal members 112 disposed within a covering 110 and fixed or slidably disposed about a core wire 128; the first member 120 being affixed to the distal end of the cannula 102, and the distal-most member 122 being affixed to the distal tip 130 of the core wire 128.

In some forms of the invention, some of the members 112 may be radiopaque to allow for more precise guidance and placement within the vasculature.

Additionally, in some forms of the invention, some of the members 112 may have magnetic properties such that they may be guided through the vasculature by an externally-applied magnetic field.

To provide for a smooth external surface of the flexible portion 108, and to prevent the bead-like structures of this invention separating from the core wire while inside a patient's vasculature, the entire flexible region of the wire guide is encapsulated within a covering which is closed at its most distal end, and affixed about the distal end of the cannula.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:
1. A wire guide to access a body vessel of a patient comprising:
   a cannula having a proximal end and a distal end, the cannula having a first lumen formed through the proximal and distal ends and having a plurality of cuts to allow the cannula to extend, defining variable rigidity;
   a flexible portion comprising a covering and a plurality of members disposed in the covering, the covering having an open end extending to a closed end, the open end attached about the distal end of the cannula, the plurality of members including a first body attached to the distal end of the cannula and a second body disposed at the closed end of the covering, the distal end of the cannula being directly attached to an outer surface of the first body, the members having apertures defining a second lumen in axial alignment with the first lumen;
   a core wire having a distal tip and being slidably disposed through the first lumen and the second lumen, the distal tip being attached to the second body.
2. The wire guide of claim 1 further comprising a first configuration having a first rigidity wherein the cuts are unextended.
3. The wire guide of claim 2 further comprising, a second configuration having a second rigidity wherein the cuts are extended, the second rigidity being less than the first rigidity.
4. The wire guide of claim 1, wherein at least one of the plurality of members comprises a magnetically responsive material for magnetically accessing the body vessel of the patient, the magnetically responsive material being one of a permanent magnet, a paramagnetic material, and a diamagnetic material.
5. The wire guide of claim 1 wherein at least one of the plurality of members comprises a radiopaque material for imaging guidance.
6. The wire guide of claim 1, wherein the first lumen has a first diameter, and the second lumen has a second diameter smaller than the first diameter.
7. An assembly for accessing a body vessel, the assembly comprising:
   a wire guide comprising:
      a cannula having a proximal end and a distal end, the cannula having a first lumen formed through the proximal and distal ends and having a plurality of cuts to allow the cannula to extend, defining variable rigidity;
      a flexible portion comprising a covering and a plurality of members disposed in the covering, the covering having an open end extending to a closed end, the open end attached about the distal end of the cannula, the plurality of members including a first body attached to the distal end of the cannula and a second body disposed at the closed end of the covering, the distal end of the cannula being directly attached to an outer surface of the first body, the members having apertures defining a second lumen in axial alignment with the first lumen;
      a core wire having a distal tip and being slidably disposed through the first lumen and the second lumen, the distal tip being attached to the second body;
   an outer sheath having a proximal section extending to a distal section, the outer sheath having a sheath lumen formed therein through the proximal and distal sections, the wire guide being disposed within the sheath lumen and the outer sheath being configured to translate axially relative to the wire guide.
8. The assembly for accessing a body vessel of claim 7 further comprising a first configuration having a first rigidity wherein the cuts are unextended.
9. The assembly for accessing a body vessel of claim 8 further comprising, a second configuration having a second rigidity wherein the cuts are extended, the second rigidity being less than the first rigidity.
10. The assembly for accessing a body vessel of claim 7, wherein at least one of the plurality of members comprises a magnetically responsive material for magnetically access- ing the body vessel of the patient, the magnetically responsive material being one of a permanent magnet, a paramagnetic material, and a diamagnetic material.

11. The assembly for accessing a body vessel of claim 7 wherein at least one of the plurality of members comprises a radiopaque material for imaging guidance.

12. The assembly of claim 7, wherein the first lumen has a first diameter, and the second lumen has a second diameter smaller than the first diameter.

13. A method of accessing a body vessel, the method comprising:
    providing an assembly comprising:
        a wire guide comprising:
            a cannula having a proximal end and a distal end, the cannula having a first lumen formed through the proximal and distal ends and having a plurality of cuts to allow the cannula to extend, defining variable rigidity;
            a flexible portion comprising a covering and a plurality of members disposed in the covering, the covering having an open end extending to a closed end, the open end attached about the distal end of the cannula, the plurality of members including a first body attached to the distal end of the cannula and a second body disposed at the closed end of the covering, the distal end of the cannula being directly attached to an outer surface of the first body, the members having apertures defining a second lumen in axial alignment with the first lumen;
            a core wire having a distal tip and being slidably disposed through the first lumen and the second lumen, the distal tip being attached to the second body; and
            an outer sheath having a proximal section extending to a distal section, the outer sheath having a sheath lumen formed therein through the proximal and distal sections, the wire guide being disposed within the sheath lumen and the outer sheath being configured to translate axially relative to the wire guide;
    introducing the outer sheath to the body vessel;
    inserting the wire guide through the outer sheath;
    varying the rigidity of the cannula; and
    navigating the wire guide through the body vessel to a treatment location.

14. The method of claim 13 wherein the varying comprises providing a first tension to the core wire such that the flexible portion is in a first configuration having a first rigidity wherein the cuts are unextended.

15. The method of claim 13 wherein varying further comprises providing a second tension, less than the first tension, to the core wire such that the flexible portion is in a second configuration having a second rigidity less than the first rigidity.

16. The method of navigating the wire guide of claim 13 further comprising locating with imaging guidance, the distal tip portion of the wire guide.

17. The method of claim 13 wherein the method further comprises navigating, with imaging guidance, the wire guide by manipulating the wire guide through the body vessel.

18. The method of claim 13, wherein the method further comprises manipulating the wire guide through the body vessel by applying a magnetic field to the flexible portion of the wire guide; and wherein at least one of the plurality of members comprises a magnetically responsive material.

19. The method of claim 18 wherein the navigating comprises applying a magnetic field to the magnetically responsive material.

20. The method of claim 18 further comprising, advancing, with imaging guidance, the flexible distal tip by manipulating the magnetic field and by advancing the wire guide through the body vessel.

* * * * *